United States Patent [19]

Satow et al.

[11] Patent Number: 5,154,755

[45] Date of Patent: * Oct. 13, 1992

[54] URACIL DERIVATIVES AND HERBICIDES CONTAINING THE SAME AS ACTIVE INGREDIENT

[75] Inventors: Jun Satow; Kenzou Fukuda; Kaoru Itoh, all of Funabashi; Koichi Suzuki, Urawa; Tsutomu Nawamaki, Yono; Shigeomi Watanabe, Omiya, all of Japan

[73] Assignee: Nissan Chemical Industries Ltd., Tokyo, Japan

[*] Notice: The portion of the term of this patent subsequent to Jan. 28, 2009 has been disclaimed.

[21] Appl. No.: 702,376

[22] Filed: May 20, 1991

Related U.S. Application Data

[63] Continuation-in-part of Ser. No. 639,216, Jan. 9, 1991, Pat. No. 5,084,084, which is a continuation-in-part of Ser. No. 549,140, Jul. 6, 1990, abandoned.

[30] Foreign Application Priority Data

| Jul. 14, 1989 | [JP] | Japan | 1-181824 |
| Jul. 19, 1989 | [JP] | Japan | 1-187065 |
| Oct. 20, 1989 | [JP] | Japan | 1-274662 |
| Jun. 27, 1990 | [JP] | Japan | 2-168683 |
| Dec. 5, 1990 | [JP] | Japan | 2-400475 |

[51] Int. Cl.$^5$ .................. C07D 239/55; A01N 43/54
[52] U.S. Cl. ................................. 71/92; 544/310
[58] Field of Search .......................... 544/311; 71/92

[56] References Cited

U.S. PATENT DOCUMENTS

| 4,358,591 | 11/1982 | Kohn | 544/311 |
| 4,746,352 | 5/1988 | Wenger et al. | 71/90 |
| 4,760,163 | 7/1988 | Wenger et al. | 71/90 |
| 4,859,229 | 8/1989 | Wenger et al. | 71/92 |
| 4,927,451 | 5/1990 | Brouwer et al. | 71/92 |
| 4,941,909 | 7/1990 | Wenger et al. | 71/92 |
| 4,979,982 | 12/1990 | Brouwer et al. | 71/92 |
| 5,017,211 | 5/1991 | Wenger et al. | 71/92 |
| 5,041,156 | 8/1991 | Suchy et al. | 71/92 |

FOREIGN PATENT DOCUMENTS

| 0195346 | 9/1986 | European Pat. Off. |
| 0255047 | 2/1988 | European Pat. Off. |
| 0311135 | 4/1989 | European Pat. Off. |
| 0408382 | 1/1991 | European Pat. Off. |

Primary Examiner—Cecilia Tsang
Attorney, Agent, or Firm—Oblon, Spivak, McClelland, Maier & Neustadt

[57] ABSTRACT

Disclosed herein is uracil derivatives having a trifluoromethyl group at the 6-position and a phenyl group at the 3-position which has a $NHSO_2D^{26}$ group at 5-position of the benzene ring, halogen atom at 4-position thereof and hydrogen atom or halogen atom at 2-position thereof, which are represented by the formula (I) and showing penetrative translocation activity, a very high herbicidal activity and, particularly, no phytotoxicity against soybean, in which as compared with the conventional herbicidal compounds, the said uracil derivatives can be applied for either soil treatment or soil incorporation treatment, thereby producing a quick and high herbicidal effect even at a very low dosage against a large variety of weeds including perennial weeds, and have the property to residual effect for an appropriate period of time.

11 Claims, No Drawings

URACIL DERIVATIVES AND HERBICIDES CONTAINING THE SAME AS ACTIVE INGREDIENT

CROSS-REFERENCE TO RELATED APPLICATION

The present application is a continuation-in-part application of Ser. No. 07/639,216 filed on Jan. 9, 1991 now U.S. Pat. No. 5,084,084 which is a continuation-in-part application of Ser. No. 07/549,140 filed on Jul. 6, 1990, now abandoned.

BACKGROUND OF THE INVENTION the present invention relates to novel uracil derivatives and herbicides having an selectivity and containing the uracil derivatives as active ingredients.

A large variety of herbicides have been prepared and practically used for protecting important crop plants such as rice, soybean, wheat, corn, cotton, beet, etc., from weeds and for enhancing productivity of these crop plant. The herbicides may be roughly classified into the following three types according to the locality of application: ① herbicides for upland cropping, ② herbicides for paddy field and ③ herbicides for non-arable land. Each kind of herbicides can be further classified into subclasses such as soil incorporation treatment type, pre-emergence treatment type and post-emergence treatment type (foilage treatment) according to the method of application.

With increase of global population in recent years, there is no denying the fact that productivity of principal crop plants gives a serious influence to food economy of each country, and thus enhancement of productivity of principal crop plants is now a matter of paramount importance. In fact, for the people engaged in farming, it is still more necessary to develop herbicides which are capable of economical and efficient killing or controlling of growth of weeds which do harm to cultivation of crop plants.

As such herbicides, there are demanded the ones which can meet the following requirements:

(1) Herbicidal effect is high with small amount of application. (It is necessary, especially from the viewpoint of environmental protection, to kill the weeds by application of as small as amount of herbicide as possible.)
(2) Residual effect is appropriate. (Recently, the problem is pointed out that the chemicals retaining their effect in soil for a long time could give damage to the next crop plants. It is thus important that the chemicals keep an appropriate residual effect after application).
(3) Weeds are killed quickly after application. (It is made possible to perform seeding and transplantation of the next crop plant in a short time after chemicals treatment.)
(4) The number of times of herbicide treatment (application) required is small. (It is of much account for the farmers that the number of times of weed-controlling work be minimized.)
(5) Weeds killed or controlled by one of herbicide is of wide range. (It is desirable that different weeds such as broad-leaved weeds, graminaceous weeds and perennial weeds can be killed or controlled by application of one of herbicides.)
(6) The application method is diversified. (The herbicidal effect is intensified when it can be applied in various ways, such as soil treatment, foliage treatment, etc.)
(7) No damage to crop plants is given. (In a cultivated field where both crop plants and weeds co-exist, it is desirable that weeds alone are killed selectively by a herbicide.)

Nevertheless, there is yet available no herbicide which can meet all of the above requirements.

It is known that certain compounds of uracil derivatives have a herbicidal activity. For instance, in the Pesticide Manual, 8th Ed., p. 89 (published by The British Crop Protection Council, 1987), Bromacil as one the herbicides having uracil skeleton is disclosed.

There are also known the following hetero-ring derivatives which can serve as active ingredient for herbicides:

(1) 3-Aryluracil-alkyl, alkenyl and alkinylenol ethers represented by the following general formula:

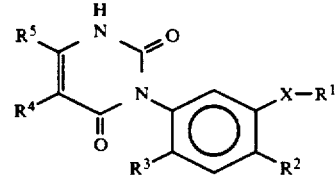

wherein $R^1$ represents $C_{1-8}$ alkyl, $C_{2-6}$ alkenyl, $C_{2-6}$ alkynyl, $C_{2-8}$ alkoxyalkyl or n

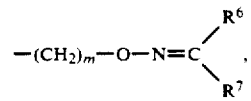

$R^2$ represents halogen or cyano, $R^3$ represents hydrogen or halogen, $R^4$ represents hydrogen, fluorine or $C_{1-4}$ alkyl, $R^5$ represents $C_{1-4}$ alkyl or $C_{1-4}$ haloalkyl, or $R^4$ and $R^5$ may combine to represent tri- or tetra-methylene (in which $R^6$ and $R^7$ represent independently $C_{1-4}$ aklyl, and m is 1 or 2), and X is O, O—C(O), O—C(O)—O or C(O)—O (Japanese Patent Application Laid-Open (Kokai) No. 64-107967).

(2) Compounds represented by the following general formula:

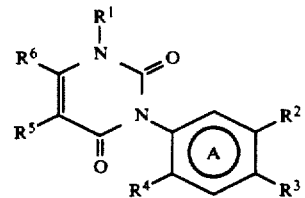

wherein $R^1$ represents hydrogen, $C_{1-4}$ alkyl, $C_{1-4}$ haloalkyl, formyl or $C_{2-6}$ alkanonyl, $R^2$ represents ether or a residue containing (thio)carbonyloxy or sulfonyloxy, the residue being directly linked to benzene nucleus A through oxygen atom, $R^3$ represents halogen or cyano, $R^4$ represents hydrogen or halogen, $R^5$ represents hydrogen, halogen or $C_{1-4}$ alkyl, and $R^6$ represents $C_{1-4}$ alkyl or $C_{1-4}$ haloalkyl, or $R^5$ and $R^6$ may be combined together to represent tri- or tetrametylene, and salts of the compounds of the said formula wherein $R^1$ is hydrogen (Japanese Patent Application Laid-Open (Kokai) No. 63-41466).

(3) Compounds represented by the following formula:

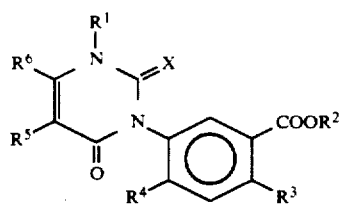

wherein $R^1$ represents hydrogen, $C_{1-4}$ alkyl, $C_{2-4}$ alkenyl, $C_{2-4}$ alkynyl, $C_{2-6}$ alkoxyalkyl, formyl, $C_{2-6}$ alkanoyl or $C_{2-6}$ alkoxycarbonyl; $R^2$ represents hydrogen, $C_{1-6}$ alkyl, $C_{2-4}$ alkenyl, $C_{2-4}$ alkynyl or $C_{2-6}$ alkoxyalkyl; $R^3$ represents halogen or nitro; $R^4$ represents hydrogen or halogen; $R^5$ represents hydrogen, halogen, $C_{1-4}$ alkyl, chloromethyl, bromomethyl, hydroxymethyl ($C_{1-5}$ alkoxy)methyl, ($C_{1-5}$ alkylthio)methyl, cyano, nitro or thiocyanato; $R^6$ represents hydrogen, $C_{1-4}$ alkyl or $C_{1-4}$ fluoroalkyl, or $R^5$ and $R^6$ are combined to represent trior tetramethylene, in which one of the said methylene groups may be substituted with oxygen or sulfur, or these groups may be substituted with $C_{1-3}$ alkyl; and X represents oxygen or sulfur, in which (i) when $R^5$ is fluorine, $R^6$ is $C_{1-4}$ alkyl or $C_{1-4}$ fluoroalkyl, and (ii) when $R^5$ is cyano, $R^6$ is hydrogen or $C_{1-4}$ alkyl, and X is oxygen, and salts of the compounds of the said formula wherein $R^1$ and/or $R^2$ represent (s) hydrogen (Japanese Patent application Laid-Open (Kokai) No. 61-221178).

(4) Herbicidal compounds having the general formula:

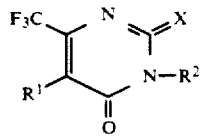

wherein X is hydrogen or hydroxy, $R^1$ is hydrogen or halo and $R^2$ is alkyl, cycloalkyl, phenyl, alkenyl, and substituted derivatives of the above (U.S. Pat. No. 3,981,715).

(5) Herbicidal compounds having the general formula:

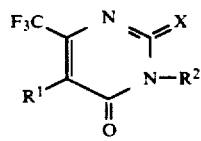

wherein X is hydrogen or hydroxy, $R^1$ is hydrogen or halo and $R^2$ is alkyl, cycloalkyl, phenyl, alkenyl, and substituted derivatives of the above (U.S. Pat. No. 3,869,457).

(6) Compounds of formula (I):

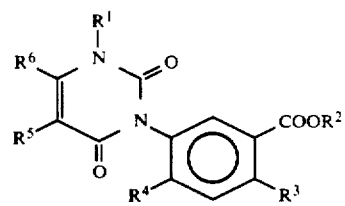

wherein $R^1$ represents hydrogen, $C_{1-4}$ alkyl, $C_{3-4}$ alkenyl, $C_{3-4}$ alkynyl, $C_{1-4}$ haloalkyl, $R^2$ represents

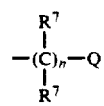

or, when $R^1$ represents haloalkyl, hydrogen, $C_{1-8}$ alkyl, $C_{2-8}$ alkenyl, $C_{2-8}$ alkynyl or $C_{2-8}$ alkoxyalkyl, $R^3$ represents halogen or cyano, $R^4$ represents hydrogen or halogen and $R^5$ represents hydrogen, fluorine or $C_{1-4}$ haloalkyl, as well as their enol ethers and salts (WO 88/10254).

Keen request is heard for the presentation of a herbicide which can meet the above-mentioned requirements (1)-(7), namely a herbicide which shows selectivity in potency, with no fear of giving any damage to crop plants (crop injury), exhibits excellent herbicidal effect at low dosage against a vide variety of weeds, and is also capable of exhibiting desired effect in both soil treatment and foliage treatment.

As a result of the present inventor's further studies, it has been found that uracil derivatives having a methyl group at 1-position of the uracil ring, a trifluoromethyl group at 6-position thereof and a phenyl group at 3-position thereof which has a $NHSO_2D^{26}$ group at 5-position of the benzene ring, a halogen atom at 4-position thereof and a hydrogen atom or a halogen atom at 2-position thereof, have a penetrative translocation activity and a high herbicidal activity at a very low dosage, and show, particularly, no phytotoxicity against soybean. Based on the finding, the present invention has been attained.

SUMMARY OF THE INVENTION

In a first aspect of the present invention, there is provided uracil derivatives represented by the formula (I):

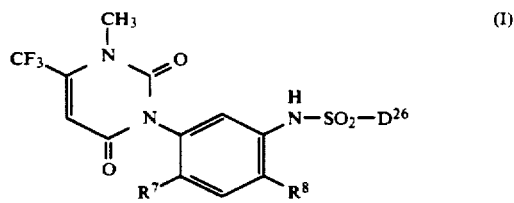

(I)

wherein $R^7$ represents hydrogen or halogen, $R^8$ represents halogen and $D^{26}$ represents Cl-4 alkyl or Cl-3 haloalkyl.

In a second aspect of the present invention, there is provided a herbicidal composition comprising a herbicidally effective amount of uracil derivatives as defined in the first aspect and a herbicidally acceptable carrier or diluent therefor.

DETAILED DESCRIPTION OF THE INVENTION

Among the uracil derivatives represented by the formula (I), uracil derivatives wherein $R^7$ represents hydrogen, fluorine or chlorine and $R^8$ represents chlorine are preferred for the object of the present invention.

Among the uracil derivatives represented by the formula (I), uracil derivative wherein $R^7$ represents hydrogen, fluorine or chlorine, $R^8$ represents chlorine and $D^{26}$ represents methyl, ethyl, n-propyl, iso-propyl, n-butyl, iso-butyl, sec-butyl, t-butyl, trifluoroethyl, chloro-n-propyl are more preferable.

The uracil derivatives of the present invention can be synthesized according to the following reaction schemes:

Scheme 1

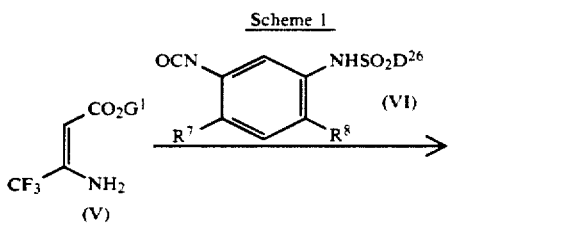

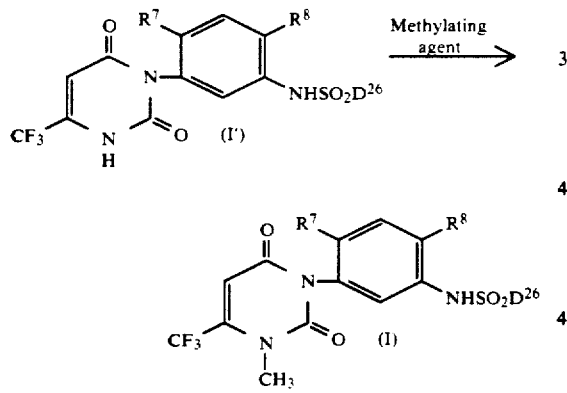

Scheme 2

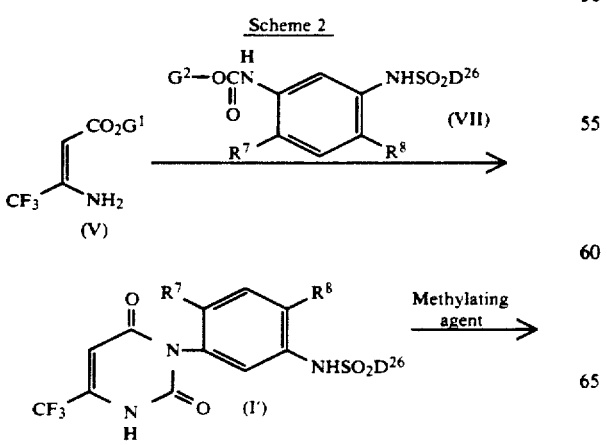

Scheme 2

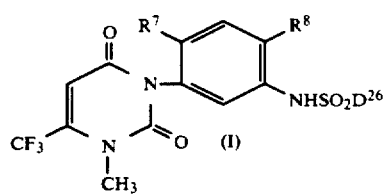

Scheme 3

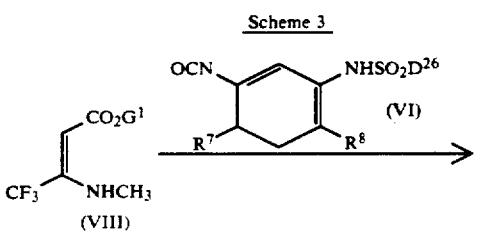

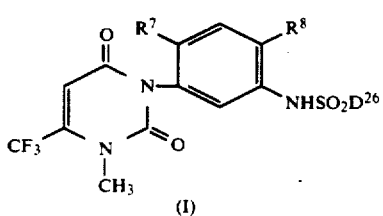

Scheme 4

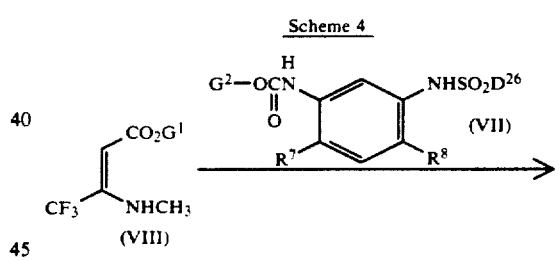

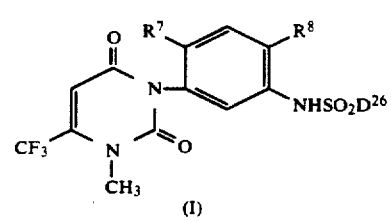

Scheme 5

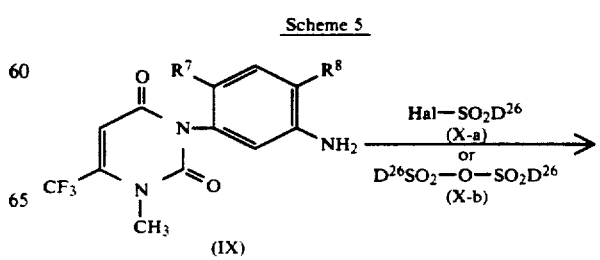

-continued
Scheme 5

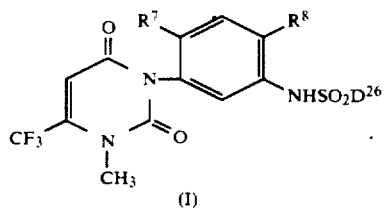
(I)

Scheme 6

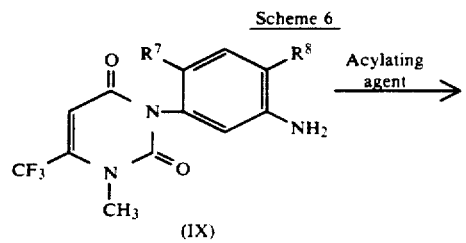
(IX)

Acylating agent →

Scheme 7

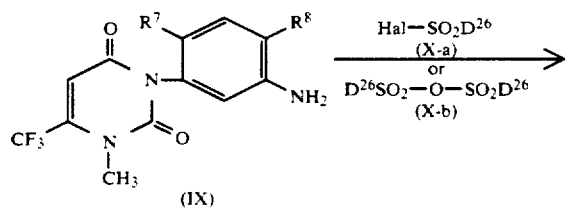
(IX)

$Hal-SO_2D^{26}$ (X-a)
or
$D^{26}SO_2-O-SO_2D^{26}$ (X-b)
→

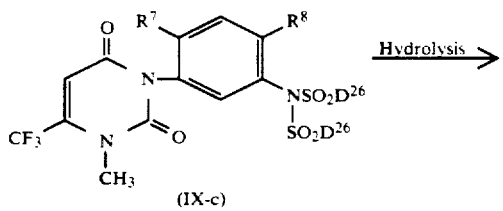
(IX-c)

Hydrolysis →

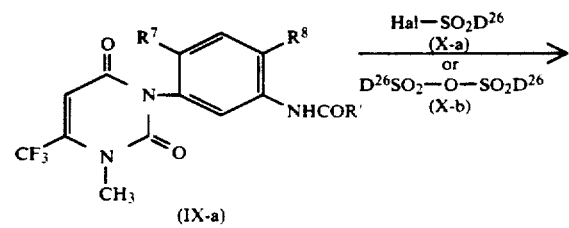
(IX-a)

$Hal-SO_2D^{26}$ (X-a)
or
$D^{26}SO_2-O-SO_2D^{26}$ (X-b)
→

-continued
Scheme 6

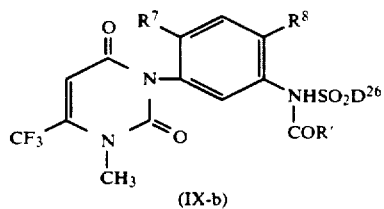
(IX-b)

Deacylation →

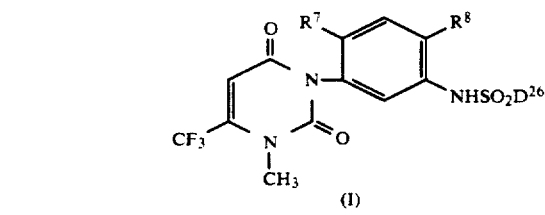
(I)

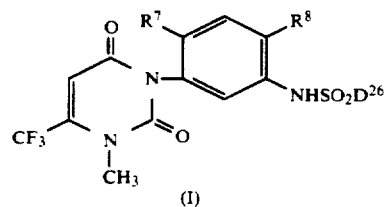
(I)

[wherein $R^7$, $R^8$ and $D^{26}$ are the same meaning as defined above, $G^1$ represents $C_{1-4}$ alkyl, $G^2$ represents $C_{1-4}$ alkyl or phenyl, R' represents hydrogen, $C_{1-4}$ alkyl or phenyl and Hal represents halogen]

(1) In Scheme 1, phenyl isocyanate (VI) is reacted with β-aminoacrylic ester (V) to form an uracil derivative (I') at the first stage, and after isolating the said derivative (I') or without isolationthereof, the 1-position of the uracil ring thereof is methylated to produce an uracil derivative of the formula (I) at the second stage.

Reaction in the first stage

Usually phenyl isocyanate (VI) is used in an amount of 0.5 to 1.5 equivalents, preferably 0.8 to 1.2 equivalents to β-aminoacrylic ester (V).

The reaction can proceed without solvent, but usually a solvent is used to accelerate the reaction. As the solvents usable for the said purpose in the reaction, aliphatic hydrocarbons such as hexane, heptane, ligroine and petroleum ether; aromatic hydrocarbons such as benzene, toluene, xylene and chlorobenzene; halogenated hydrocarbons such as chloroform and methylene chloride; ethers such as diethyl ether, dioxane and tetrahydrofuran; ketones such as acetone and methyl ethyl ketone; nitriles such as acetonitrile and isobutyronitrile; tertiary amines such as pyridine and N,N-diethylaniline; acid amides such as N,N-dimethylacetamide, N,N-dimethylformamide and N-methylpyrrolidone; sulfur-containing compounds such as dimethyl sulfoxide and sulfolane; water; and mixtures thereof may be exemplified. Among them, the aliphatic hydrocarbons, the aromatic hydrocarbons, the acid amides, the sulfur-containing compounds and mixtures thereof are preferred.

The reaction can proceed without base, but usually a base is used in an amount of 0.5 to 10 equivalents, preferably 1.0 to 3.0 equivalents to β-aminoacrylic ester (V). As the base, there can be used, for instance, organic bases containing nitrogen such as pyridine, triethylamine, N,N-dimethylaniline, N,N-diethylaniline, 4-(N,N-dimethylamino)pyridine and 1,4-diazabicyclo[2,2,2]octane; inorganic bases such as sodium hydride, potassium hydride, sodium hydroxide, potassium hydroxide, sodium carbonate and potassium carbonate; and metal alcoholates such as sodium methoxide, sodium ethoxide and potassium-tert-butoxide. Among them, sodium hydride, sodium hydroxide and potassium hydroxide are preferred.

Reaction temperature is usually from −70° to 200° C., preferably from −30° C. to reflux temperature of the reaction mixture.

Reaction time is usually 5 minutes to 72 hours, preferably 10 minutes to 12 hours.

After the reaction is completed, the derivative (I') can be isolated by making the reaction product acidic with a mineral acid such as hydrochloric acid or an organic acid such as acetic acid, trifluoroacetic acid, p-toluenesulfonic acid or the like.

Reaction in the second stage

In the second stage of reaction, the derivative (I') is methylated by using a methylating agent in an amount of 0.5 to 10 equivalents, preferably 0.8 to 5.0 equivalents to the derivative (I'). As the methylating agent, there can be used, for instance, dimethylsulfuric acid, and methyl halides such as methyl chloride, methyl bromide and methyl iodide.

The reaction can proceed without solvent, but usually a solvent is used to accelerate the reaction. As the solvents usable for the said purpose in the above reaction, aliphatic hydrocarbons such as hexane, heptane, ligroine and petroleum ether; aromatic hydrocarbons such as benzene, toluene, xylene and chlorobenzene; halogenated hydrocarbons such as chloroform and methylene chloride; ethers such as diethyl ether, dioxane and tetrahydrofuran; ketones such as acetone and methyl ethyl ketone; nitriles such as acetonitrile and isobutyronitrile; tertiary amines such as pyridine and N,N-diethylaniline; acid amides such as N,N-dimethylacetomide, N,N-dimethylformamide and N-methylpyrrolidone; sulfur-containing compounds such as dimethyl sulfoxide and sulfolane; water and mixtures thereof may be exemplified. Among them, the aliphatic hydrocarbons, the aromatic hydrocarbons, the ethers, the ketones, the nitriles, the acid amides, the sulfur-containing compounds and mixtures thereof are preferred.

In the above reaction, usually a base is used in an amount of 0.5 to 10 equivalents, preferably 0.8 to 3.0 equivalents to the derivative (I'). As the base, there can be used organic bases containing nitrogen such as pyridine, triethylamine, N,N-dimethylaniline, N,N-diethylaniline, 4-(N,N-dimethylamino)pyridine and 1,4-diazabicyclo[2,2,2]octane; and inorganic bases such as sodium hydride, potassium hydride, sodium hydroxide, potassium hydroxide, sodium carbonate and potassium carbonate. Among them, such inorganic bases as sodium hydride and potassium carbonate are preferred.

Reaction temperature is usually from −30° to 150° C., preferably from −10° C. to reflux temperature of the reaction mixture.

Reaction time is usually 10 minutes to 96 hours, preferably 30 minutes to 48 hours.

(2) According to Scheme 2, N-phenyl carbamate (VII) is reacted with β-aminoacrylic ester (V) to form an uracil derivative (I') at the first stage, and after isolating the derivative (I') or without isolation thereof, the 1-position of the uracil ring thereof is methylated to produce an uracil derivative of the formula (I) at the second stage.

Reaction in the first stage

Usually N-phenyl carbamate (VII) is used in an amount of 0.5 to 1.5 equivalents, preferably 0.8 to 1.2 equivalents to β-aminoacrylic ester (V).

Usually a solvent is required to be present in the reaction. As the solvent, there can be used, for instance, aliphatic hydrocarbons such as hexane, heptane, ligroine and petroleum ether; aromatic hydrocarbons such as benzene, toluene, xylene and chlorobenzene; halogenated hydrocarbons such as chloroform and methylene chloride; ethers such as diethyl ether, dioxane and tetrahydrofuran; ketones such as acetone and methyl ethyl ketone; nitriles such as acetonitrile and isobutyronitrile; tertiary amines such as pyridine and N,N-diethylaniline; acid amides such as N,N-dimethylacetamide, N,N-dimethylformamide and N-methylpyrrolidone; sulfur-containing compounds such as dimethyl sulfoxide and sulfolane; alcohols such as methanol, ethanol, propanol and butanol; water; and mixtures thereof. Among them, the aliphatic hydrocarbons, the aromatic hydrocarbons, the acid amides, the sulfur-containing compounds and mixtures thereof are preferred.

In the above reaction, usually a base is used in an amount of 0.5 to 10 equivalents, preferably 1.0 to 3.0 equivalents to β-aminoacrylic ester (V). The bases usable in the above reaction include organic bases containing nitrogen such as pyridine, triethylamine, N,N-dimethylaniline, N,N-diethylanilin, 4-(N,N-dimethylamino)pyridine and 1,4-diazabicyclo[2,2,2]octane; inorganic bases such as sodium hydride, potassium hydride, sodium hydroxide, potassium hydroxide, sodium carbonate and potassium carbonate; metal alcoholates such as sodium methoxide, sodium ethoxide and potassium-tert-butoxide; and metal alkyl mercaptides such as sodium methyl mercaptide and sodium ethyl mercaptide. Among them, inorganic bases such as sodium hydride and metal alcoholates such as sodium methoxide are preferred.

The reaction is carried out at a temperature of usually from 0° to 200° C., preferably from room temperature to reflux temperature of the reaction mixture.

Reaction time is usually 10 minutes to 24 hours, preferably 30 minutes to 24 hours.

After the completion of the reaction, the derivative (I') can be isolated from the reaction mixture by acidifying it with a mineral acid such as hydrochloric acid or an organic acid such as acetic acid, trifluoroacetic acid and p-toluenesulfonic acid.

Reaction in the second stage

Methylation of the derivative (I') can be effectuated under the same reaction conditions as in the second stage of Scheme 1.

(3) In Scheme 3, phenyl isocyanate (VI) is reacted with N-methyl-β-aminoacrylic ester (VIII) to produce an uracil derivative of the formula (I) in a single stage. It is possible to employ the same reaction conditions as used in Scheme 1.

(4) In Scheme 4,N-phenyl carbamate (VII) is reacted with N-methyl-β-aminoacrylic ester (VIII) to produce an uracil derivative of the formula (I) in a single stage. The reaction can be performed under the same reaction conditions as used in Scheme 2.

(5) In Scheme 5, a sulfonylhalide (X-a) or a sulfonic anhydride (X-b) is reacted with an aminated compound (IX) to produce an uracil derivative of the formula (I) in a single stage.

Usually the sulfonylhalide (X-a) or sulfonic anhydride (X-b) is used in amount of 0.3 to 10 equivalents, preferably 0.5~2.0 equivalents to the aminated compound (IX).

The reaction can proceed without solvent, but usually a solvent is used to accelerate the reaction. As the solvents usable for the said purpose in the reaction, aliphatic hydrocarbons such as hexane, heptane, ligroine and petroleum ether; aromatic hydrocarbons such as benzene, toluene, xylene and chlorobenzene; halogenated hydrocarbons such as chloroform and methylene chloride; ethers such as diethyl ether, dioxane and tetrahydrofuran; ketones such as acetone and methyl ethyl ketone; nitriles such as acetonitrile and isobutyronitrile; tertiary amines such as pyridine and N,N-diethylaniline; acid amides such as N,N-dimethylacetamide, N,N-dimethylformamide and N-methylpyrrolidone; sulfur-containing compounds such as dimethyl sulfoxide and sulfolane; and mixtures thereof.

The reaction can proceed without base, but usually a base is used in an amount of 0.3 to 10 equivalents to the aminated compound (IX). Also, the base may be used in large excess as the solvent. As the base, there can be used, for instance, organic bases containing nitrogen such as pyridine, triethylamine, N,N-dimethylaniline, N,N-diethylaniline, 4-(N,N-dimethylamine)pyridine and 1,4-diazabicyclo[2,2,2]octane; inorganic bases such as sodium hydride, potassium hydride, sodium hydroxide, potassium hydroxide, sodium carbonate and potassium carbonate; and metal alcoholates such as sodium methoxide, sodium ethoxide and potassium-tert-butoxide. Among them, the organic bases containing nitrogen and the inorganic bases are preferred.

Reaction temperature is usually from −30° to 160° C., preferably from −10° to 130° C.

Reaction time is usually 10 minutes to 48 hours, preferably 30 minutes to 24 hours.

(6) In Scheme 6, an aminated compound (IX) is reacted with an acylating agent to form an acylated amino compound (IX-a) at the first stage; after isolating the acylated amino compound (IX-a) or without isolation thereof, the acylated amino compound (IX-a) is sulfonylated to produce an N-acylsulfamoylated compound (IX-b) in the second stage; and after isolating the N-acylsulfamoylated compound (IX-b) or without isolation thereof, the N-acylsulfamoylated compound (IX-b) is deacylated to produce an uracil derivative of the formula (I) at the third stage.

Reaction in the first stage

Usually an acylating agent is used in an amount of 0.5 to 5.0 equivalents, preferably 0.8 to 2.0 equivalents to the aminated compound (IX). As the acylating agent, acetyl chloride, benzoyl chloride, acetic anhydride and formic acid are usable and acetic anhydride is preferable.

The reaction can proceed without solvent, but usually a solvent is used to accelerate the reaction. As the solvents usable for the said purpose in the reaction, aliphatic hydrocarbons such as hexane, heptane, ligroine and petroleum ether; aromatic hydrocarbons such as benzene, toluene, xylene and chlorobenzene; halogenated hydrocarbons such as chloroform and methylene chloride; tertiary amines such as pyridine and N,N-diethylaniline; acid amides such as N,N-dimethylacetamide, N,N-dimethylformamide and N-methylpyrrolidone; sulfur-containing compounds such as dimethyl sulfoxide and sulfolane; organic acids such as formic acid, acetic acid and butyric acid; and mixtures thereof may be exemplified. Among them, the aliphatic hydrocarbons, the aromatic hydrocarbons, the halogenated hydrocarbons and the organic acid are preferred.

The reaction can proceed without base, but usually a base is used in an amount of 0.5 to 5.0 equivalents, preferably 0.8 to 2.0 equivalents to the aminated compound (IX). As the base, there can be used, for instance, organic bases containing nitrogen such as pyridine, triethylamine, N,N-dimethylaniline, N,N-diethylaniline, 4-(N,N dimethylamino)pyridine and 1,4-diazabicyclo[2,2,2]octane; inorganic bases such as sodium hydride, potassium hydride, sodium hydroxide, potassium hydroxide, sodium carbonate and potassium carbonate; and acetic acid salts such as sodium acetate and potassium acetate.

Reaction temperature is usually from −30° to 200° C., preferably from 0° to 130° C.

Reaction time is usually 10 minutes to 24 hours, preferably 30 minutes to 6 hours.

Reaction in the second stage

In the second stage of reaction, an acylated amino compound (IX-a) is sulfonylated by using a sulfonylating agent in an amount of 0.5 to 5.0 equivalents, preferably 0.8 to 2.0 equivalents to the acylated amino compound (IX-a). As the sulfonylating agent, there can be used, for instance, sulfonylhalide represented by the formula: Hal-SO$_2$D$^{26}$ (X-a) and sulfonic anhydride represented by the formula: D$^{26}$SO$_2$—O—SO$_2$D$^{26}$ (X-b).

The reaction can proceed without solvent, but usually a solvent is used to accelerate the reaction. As the solvents usable for the said purpose in the above reaction, aliphatic hydrocarbons such as hexane, heptane, ligroine and petroleum ether; aromatic hydrocarbons such as benzene, toluene, xylene and chlorobenzene; halogenated hydrocarbons such as chloroform and methylene chloride; ethers such as diethyl ether, dioxane and tetrahydrofuran; ketones such as acetone and methyl ethyl ketone; nitriles such as acetonitrile and isobutyronitrile; tertiary amines such as pyridine and N,N-diethylaniline; acid amides such as N,N-dimethylacetamide, N,N-dimethylformamide and N-methylpyrrolidone; sulfur-containing compounds such as dimethyl sulfoxide and sulfolane; and mixtures thereof may be exemplified.

In the above reaction, usually a base is used in an amount of 0.5 to 5.0 equivalents, preferably 0.8 to 2.0 equivalents to the acylated amino compound (IX-a). As the base, there can be used organic bases containing nitrogen such as pyridine, triethylamine, N,N-dimethylaniline, N,N-diethylaniline, 4-(N,N-dimethylamino)pyridine and 1,4-diazabicyclo[2,2,2]octane; inorganic bases such as sodium hydride, potassium carbonate and potassium carbonate and metal alcoholates such as sodium methoxide, sodium ethoxide and potassium-tert-butoxide. Among them, the organic bases containing nitrogen and inorganic bases are preferred.

Reaction temperature is usually from −30° to 160° C., preferably from −10° to 130° C.

Reaction time is usually 30 minutes to 48 hours, preferably 1 to 12 hours.

Reaction in the third stage

Usually water, alkalis or acids is used in amount of 0.5 to 3.0 equivalents, preferably 0.8 to 2.0 equivalents to the N-acylsulfamoylated compound (IX-b).

As the alkalis, inorganic bases such as sodium hydride, potassium hydride, sodium hydroxide, potassium hydroxide, sodium carbonate and potassium carbonate; and metal alcoholates such as sodium methoxide, sodium ethoxide and potassium-tert-butoxide may be exemplified. Among them, the inorganic bases are preferred.

As the acids, inorganic acids such as hydrochloric acid and sulfuric acid; and organic acids such as acetic acid and trifluoroacetic acid may be exemplified.

The reaction can proceed without solvent, but usually a solvent is used to accelerate the reaction. As the solvent, there can be used, for instance, aliphatic hydrocarbons such as hexane, heptane, ligroine and petroleum ether; aromatic hydrocarbons such as benzene, toluene, xylene and chlorobenzene; halogenated hydrocarbons such as chloroform and methylene chloride; alcohols such as methanol and ethanol; ethers such as diethyl ether, dioxane and tetrahydrofuran; ketones such acetone and methyl ethyl ketone; nitriles such as acetonitrile and isobutyronitrile; tertiary amines such as pyridine, triethylamine, N,N-dimethylaniline and N,N-diethylaniline; acid amides such as N,N-dimethylacetomide, N,N-dimethylformamide and N-methylpyrrolidone; organic acids such as formic acid, acetic acid and butyric acid; water; and mixtures thereof. Among them, the alcohols, the ethers, the ketones, the tertiary amines, the acid amides, the organic acids and water are preferred.

The reaction is carried out at a temperature of usually from −30° to 130° C., preferably from −10° to 100° C.

Reaction time is usually 10 minutes to 48 hours, preferably 30 minutes to 24 hours.

(7) In Scheme 7, an aminated compound (IX) is sulfonylated to produce a disulfonylaminated compound (IX-c) in the first stage; and after isolating the disulfonylaminated compound (IX-c) or without isolation thereof, the disulfonylaminated compound (IX-c) is hydrolyzed to produce an uracil derivative of the formula (I) at the second stage.

Reaction in the first stage

Usually a sulfonylhalide (X-a) or sulfonic anhydride (X-b) is used in an amount of 1.0 to 20 equivalents, preferably 2.0 to 5.0 equivalents to the aminated compound (IX).

The reaction can proceed without solvent, but usually a solvent is used to accelerate the reaction. As the solvents usable for the said purpose in the reaction, aliphatic hydrocarbons such as hexane, heptane, ligroine and petroleum ether; aromatic hydrocarbons such as benzene, toluene, xylene and chlorobenzene; halogenated hydrocarbons such as chloroform and methylene chloride; ethers such as diethyl ether, dioxane and tetrahydrofuran; ketones such as acetone and methyl ethyl isobutyronitrile; tertiary amines such as pyridine and N,N-diethylaniline; acid amides such as dimethylacetamide, N,N-dimethylformamide and N-methylpyrrolidone; sulfur-containing compounds such as dimethyl sulfoxide and sulfolane; and mixtures thereof may be exemplified.

The reaction can proceed without base, but usually a base is used in an amount of 1.0 to 10 equivalents, preferably 2.0 to 3.0 equivalents to the aminated compound (IX). As the base, there can be used, for instance, organic bases containing nitrogen such as pyridine, triethylamine, N,N-dimethylaniline, N,N-diethylaniline, 4-(N,N-dimethylamino)pyridine and 1,4-diazabicyclo[2,2,2]octane; inorganic bases such as sodium hydride, potassium hydride, sodium hydroxide, potassium hydroxide, sodium carbonate and potassium carbonate; and metal alcoholates such as sodium methoxide, sodium ethoxide and potassium-tert-butoxide. Among them, the organic bases containing nitrogen and inorganic bases are preferred.

The reaction is carried out at a temperature of usually from −30° to 160° C., preferably from −10° to 130° C.

Reaction time is usually 30 minutes to 60 hours, preferably 1 to 30 hours.

Reaction in the second stage

Water, alkalis or acids is used in an amount of 0.5 to 3.0 equivalents, preferably 0.8 to 2.0 equivalents to the disulfonylaminated compound (IX-c) in order to hydrolyze it.

As the alkalis, inorganic bases such as sodium hydride, potassium hydride, sodium hydroxide, potassium hydroxide, sodium carbonate and potassium carbonate; and metal alcoholates such as sodium methoxide, potassium methoxide and potassium-tert-butoxide may be exemplified. Among them, the inorganic bases are preferred.

As the acids, inorganic acids such as hydrochloric acid and sulfuric acid; and organic acids such as acetic acid and trifluoroacetic acid may be exemplified.

The reaction can proceed without solvent, but usually a solvent is used to accelerate the reaction. As the solvents usable for the said purpose in the reaction, aliphatic hydrocarbons such as hexane, heptane, ligroine and petroleum ether; aromatic hydrocarbons such as benzene, toluene, xylene and chlorobenzene; halogenated hydrocarbons such as chloroform and methylene chloride; alcohols such as methanol and ethanol; ethers such as diethyl ether, dioxane and tetrahydrofuran; ketones such as acetone and methyl ethyl ketone; nitriles such as acetonitrile and isobutyronitrile; tertiary amines such as pyridine, trimethylamine, N,N-dimethylaniline, N,N-diethylaniline 4-(N,N-dimethylamino)-pyridine and 1,4-diazabicyclo[2,2,2]octane; acid amides such as N,N-dimethylacetamide, N,N-dimethylformamide and N-methylpyrrolidone; organic acids such as formic acid, acetic acid and butyric acid; water; and mixtures thereof may be exemplified. Among them, the alcohols, the ethers, the ketones, the tertiary amines, the acid amides, the organic acids, and water are preferred.

The reaction is carried out at a temperature of usually rom −30° to 160° C., preferably −10° to 130° C.

Reaction time is usually 5 minutes to 48 hours preferably 30 minutes to 24 hours.

The uracil derivatives of the present invention can be applied as a herbicide for upland field, paddy fields and non-arable land through either soil treatment or foliage treatment. Also, they show high herbicidal activities at a low dosage against, for instance, cropland weeds of broad-leaved weeds of Solananceae weeds such as *Solanum nigrum* and *Datura stramonium*, Malvaceae weeds such as *Abutilon theophrasti* and *Side spinosa*, Convolvulaceae weeds such as *Ipomoea* spps. of *Ipomoea purpurea*, and *Calystegia* spps., Amaranghaceae weeds such as *Amaranthus lividus* and *Amaranthus retroflexus*, Compositae weeds such as *Xanthium pensylvanicum, Ambrosia artemisiaefolia, Helianthus annuus, Galinsoga ciliata, Cirsium arvense, Senecio vulgaris, Erigeron annus* and *Bidens pilosa*, Cruciferae weeds such as *Rorippa indica, Sinapis arvensis* and *Capsella Bursapastris*, Polygonaceae weeds such as *Polygonum Blume* and *Polygonum convolvulus*, Portulacaceae weeds such as *Portulaca oleracea*, Chenopodiaceae weeds such as *Chenopodium album, Chenopodium ficifolium* and *Kochias coparia*, Caryophyllaceae weeds such as *Stellaria media*, Scrophulariaceae weeds such as *Veronic persica*, Commelinaceae weeds such as *Commelina communis*, Labiatae weeds such as *Lamium amplexicaule* and *Lamium purpureum*, Euphorbiaceae weeds such as *Euphorbia supina* and *Euphorbia maculata*, Rubiaceae weeds such as *Galium spurium, Galium aparine* and *Rubiaakane*,; Violaceae weeds such as *Viola arvensis*, and Leguminosae weeds such *Sesbania exaltata* and *Cassis obtusifolia;* Graminaceous weeds such as *Sorgham bicolor, Panicum dichotomiflorum, Sorghus halepense, Echinochloa crusgalli, Digitaria adscendens, Avena fatua, Eleusine indica, Setaria viridis* and *Alopecurus aegualis;* Cyperaceous weeds such as *Cyperus rotundus* and *Cyperus esculentus;* and paddy weeds of Alismataceae weeds such as *Alisma canaliculatum, Sagittaria trifolia* and *Sagittaria pygmaea*, cyperaceae weeds such as *Cyperus difformis, Cyperus serotinus, Scirpus juncoides* and *Eleocharis kuroguwai*, Scrothulariaceae weeds such as *Lindemia pyxidaria*, Potenderiaceae weeds such as *Monochoria Vaginalis*, Potamogetonaceae weeds such as *Potamogeton distinctus*, Lythraceae weeds such as *Rotala indica* and Gramineae weeds such as *Echinochloa crus-galli.* It is also quite remarkable that the uracil derivatives of the present invention do not harm to the important crops such as wheat, corn, barley, soybean, rice. Especially, since the uracil derivatives of the present invention show no phytotoxicity against soybean through either soil treatment or soil incorporation treatment, and high herbicidal activities at a very low dosage against weeds of *Abutilon theophrasti, Xanthium pensylvanicum, Ipomoea* spps. of *Ipomoea purpurea, Calystegia* spps., *Amaranthus retroflexus, Polygonum Blume, Polygonum convolvulus, Portulaca oleracea, Chenopodium album, Datura stramonium, Ambrosia artemisiaefolia, Bidens pilosa, Side spinosa, Sebsania exaltata* and *Solanum nigrum.*

Further, the uracil derivatives of the present invention are also useful as a defoliant.

In use of the compounds of present invention as a herbicide, they are usually mixed with a carrier, for example, a solid carrier such as clay, talc, bentonite, diatomaceous earth and white carbon (fine silica powder), or a liquid carrier such as water alcohols (isopropanol, butanol, benzyl alcohol, furfuryl alcohol, etc.), aromatic hydrocarbons (toluene, xylene, etc.), ethers (anisole, etc.) ketones (cyclohexanone, isophorone, etc.), esters (butyl acetate, etc.), acid amides (N-methylpyrrolidone, etc.) and halogenated carbons (chlorobenzene, etc.). Also, if necessary, they may be added with a suitable adjuvant such as surfactant, emulsifier, dispersant, penetrating agent, spreader, thickener, anti-freezing agent, coagulation preventing agent, stabilizer and the like, and can be offered to practical use in various forms of formulation such as liquid formulation, emulsifiable concentrate, wettable powder, dry flowable, flowable, dust and granule.

In a herbicidal composition of the present invention, an amount of an active ingredient of the uracil derivative of the present invention is in the range of 01. to 90 parts by weight and an amount of a herbicidal acceptable carrier or diluent is in the range of 10 to 99.9 parts by weight, based on 100 parts by weight of the herbicidal composition.

More particularly, preferable composition ratios (based on 100 parts by weight of the herbicidal composition) of the uracil derivative of the present invention in each formulation are set forth below.

| Wettable Powder | |
|---|---|
| The uracil derivative of the present invention | 5 to 80 parts by weight |
| Solid carrier | 10 to 85 parts by weight |
| Surfactant | 1 to 10 parts by weight |
| Other carrier | 1 to 5 parts by weight |
| (For example, coagulation preventing agent, etc.) | |
| Emulsifiable Concentrate | |
| The uracil derivative of the present invention | 1~30 parts by weight |
| Liquid carrier | 30~95 parts by weight |
| Surfactant | 5~15 parts by weight |
| Flowable | |
| The uracil derivative of the present invention | 5~70 parts by weight |
| Liquid carrier | 15~65 parts by weight |
| Surfactant | 5~12 parts by weight |
| Other carrier | 5~30 parts by wei9ht |
| (For example, anti-freezing agent, thickener, etc.) | |
| Granular Wettable Powder (Dry Flowable) | |
| The uracil derivative of the present invention | 20~90 parts by weight |
| Solid carrier | 10~60 parts by weight |
| Surfactant | 1~20 parts by weight |
| Granules | |
| The uracil derivative of the present invention | 0.1~10 parts by weight |
| Solid carrier | 90~99.99 parts by weight |
| Other carrier | 1~5 parts by weight |

The compounds of present invention may be mixed, if necessary, with other kinds of herbicide, various kinds of insecticide, fungicide, plant growth regulating agent, synergism agent and the like in the course of preparation or at the time of application of the formulation.

As the kinds of herbicide that can be mixed with the compounds of present invention in use thereof, there can be mentioned, for instance, the compounds described in Farm Chemicals Handbook, 1990.

Especially, in case applying the compound of the present invention to soybean, as the preferable compound which may be mixed with the compound of the present invention, trifluralin, pendimethalin, alachlor, metolachor, metribuzin, linuron, chlorimuron ethyl, imazaquin, imazethapyr, dinoseb, bifenox and clomazone may be examplified.

The application rate of the compound of the present invention is variable depending on the place of application, time of application, method of application, kind of crop to be treated, etc., but it is usually appropriate to apply the compound of the present invention in an amount of about 0.0001 to 10 kg/ha, preferably 0.001 to 5 kg/ha measured as the amount of active ingredient.

The uracil derivatives of the present invention have an excellent penetrative translocation activity and a very high herbicidal activity at a very low dosage, and show no phytotoxicity against soybean, and can be applied through either soil treatment or soil incorporation treatment against a wise variety of weeds.

EXAMPLES

The present invention is explained in more detail in the following Examples, however, it should be recognized that the scope of the present invention is not restricted to these examples.

EXAMPLE 1

Synthesis of
3-(4-chloro-3-ethanesulfonylaminophenyl)-1-methyl-6-trifluoromethyl-2,4 (1H,3H)-pyrimidinedione
(Compound 2)

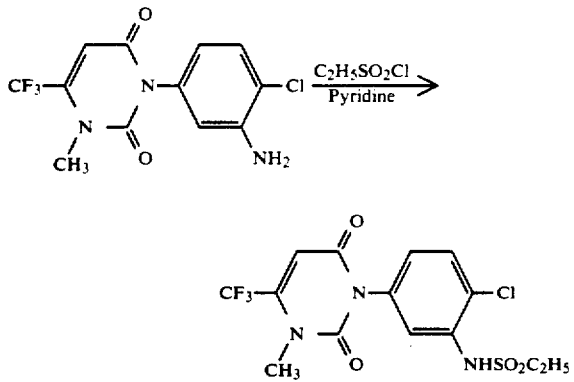

0.50 g of 3-(3-amino-4-chlorophenyl)-1-methyl-6-trifluoromethyl-2,4(1H,3H)-pyrimidimedione was dissolved in 5 ml of pyridine. To the obtained solution, 0.16 ml of ethanesulfonylchloride was added dropwise at a temperature of no higher than 5° C. and the mixed solution was stirred for 2 hours. After the reaction was completed, pyridine was distilled off and the residue was dissolved in ethyl acetate. The solution was washed with water, dilute hydrochloric acid and a saturated sodium chloride aqueous solution, and dried over anhydrous sodium sulfate, and then ethyl acetate was distilled off to obtain a crude product. The obtained product was washed with diisopropyl ether to obtain 0.37 g of the objective product as light brown crystals.

EXAMPLE 2

Synthesis of
3-(4-chloro-2-fluoro-5-isopropylsulfonylaminophenyl)-1-methyl-6-trifluoromethyl-2,4 (1H,3H)-pyrimidinedione (Compound 5)

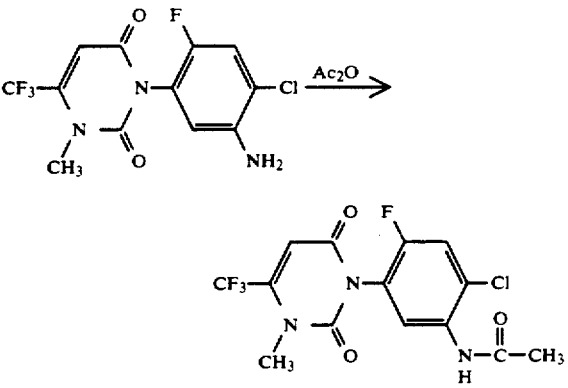

2.00 g of 3-(5-amino-4-chloro-2-fluorophenyl)-1-methyl-6-trifluoromethyl-2,4 (1H,3H)-pyrimidinedione was dissolved in 5 ml of benzene. To the obtained solution, 0.61 ml of acetic anhydride was added an the resultant solution was refluxed for one hour. After distilling off benzene, the obtained crude product was washed with hexane to obtain 3-(5-acetylamino-4-chloro-2-fluorophenyl) -1-methyl-6-trifluoromethyl-2,4(1H,3H)-pyrimidinedione as white crystals.
m.p.: 263°~266° C.
$^1$H-NMR($d_6$-DMSO) δ(ppm): 2.15(3H,s), 3,47(3H,s), 6.54(1H,s), 7.70(1H,d,J=9Hz), 7,90(1H,d,J=8Hz), 9.56(1H,br s)

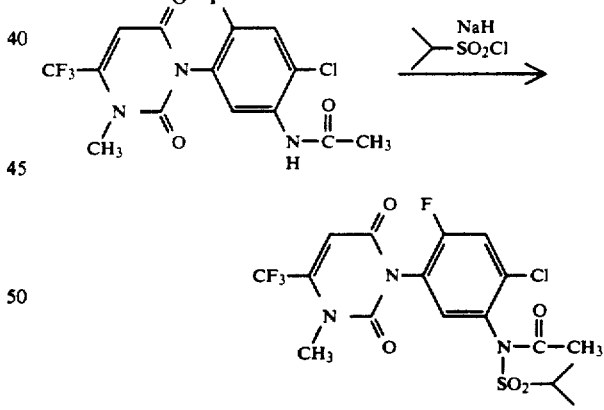

to a suspension of 0.11 g of sodium hydride (oil, purity: 60%) in 10 ml of tetrahydrofuran, 1.00 g of the obtained 3-(5-acetylamino-4-chloro-2-fluorophenyl)-1-methyl-6-trifluoromethyl-2,4 (1H,3H)-pyrimidinedione was added at a temperature of 0° C. and then 0.30 ml of isopropylsulfonylchloride was added dropwise to the resultant suspension. After stirring for 2 hrs, the reaction mixture was poured into ice water and extracted with ethyl acetate. The extract of the ethyl acetate layer was washed with a saturated sodium chloride aqueous solution and dried over anhydrous sodium sulfate. Then ethyl acetate was distilled off to obtain a crude product. The obtained product was purified by preparative thin-layer chromatography (developing solvent: hexane/ethyl acetate=2/1) to obtain 0.54 g of 3-[4-chloro-2-fluoro-5-(N-acetyl) isopropylsulfonylaminophenyl]-1-methyl-6-trifluoromethyl-2,4(1H,3H)-pyrimidinedione as a colorless viscous oil.

¹H-NMR (CDCl₃) δ(ppm): 1.45(6H, d,J=7Hz), 1.97(3H,s), 3.47(3H,s), 4,10(1H, qq,J=7Hz), 6,23(1H,s), 7.29(1H,d,J=7Hz), 7.36(1H,d,J=9Hz)

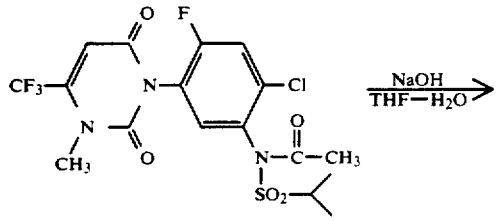

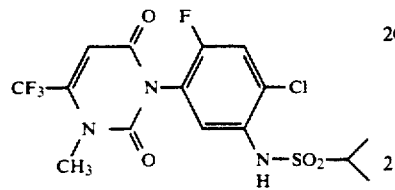

0.47 g the obtained 3-[4-chloro-2-fluoro-5-(N-acetyl) isoporopylsulfonylaminophenyl]-1-methyl-6-trifluoromethyl-2,4(1H,3H)-pyrimidienedione was dissolved in 5 ml of tetrahydrofuran. To the obtained solution, 0.04 g of sodium hydroxide and 0.06 ml of water were added and the mixed solution was stirred for 4 hours. After the reaction was completed, the reaction mixture was poured into dilute hydrochloride acid and extracted with ethyl acetate. The extract of the ethyl acetate layer was washed with water and a saturated sodium chloride aqueous solution, and dried over anhydrous sodium sulfate. Then ethyl acetate was distilled off to obtain a crude product. The obtained product was purified by preparative thin-layer chromatography (developing solvent: hexane/ethyl acetate=3/1) to obtain 0.29 g of the objective compound as a colorless viscous oil.

EXAMPLE 3

Synthesis of
3-(2,4-dichloro-5-ethanesulfonylaminophenyl)-1-methyl-6-trifluoromethyl-2,4 (1H,3H)-pyrimidinedione
(Compound 9)

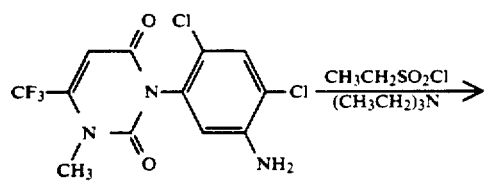

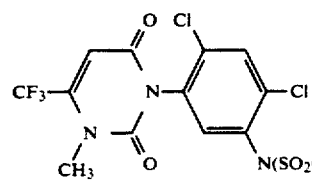

To a mixture of 1.00 g of 3-(5-amino-2,4-dichlorophenyl)-1-methyl-6trifluoromethyl-2,4 (1H,3H)-pyrimidinedione, 0.60 g of triethylamine and 10 ml of dichloromethane, 0.56 g of ethanesulfonylchloride was added at a temperature of not more than 5° C. The resultant mixture was stirred overnight. After washing twice the reaction mixture with water, the reaction mixture was washed with a saturated sodium chloride aqueous solution and dried over anhydrous sodium sulfate. The dichloromethane was distilled off to obtain a crude product. The obtained product was washed with diisopropylether to obtain 1.40 g of 3-[5-bis (ethanesulfonyl)amino-2,4-dichlorophenyl]-1-methyl-6-trifluoromethyl-2,4(1H,3H)-pyrimidinedione as light yellow crystals. m.p.: 221°~223° C.

¹H-NMR(d₆-DMSO) δ(ppm): 1.48)6H,t,J=7Hz), 3,49(3H,s), 3.61(4H,q,J=7Hz), 6,27(1H,s), 7.56(1H,s), 7.67(1H,s)

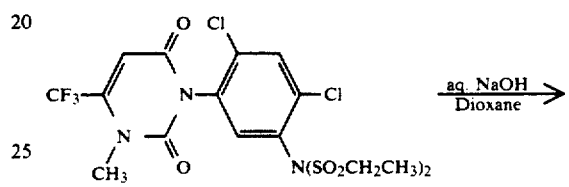

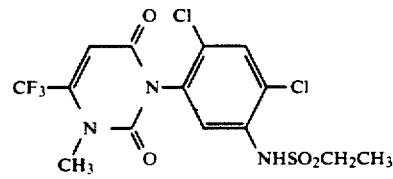

To 8 ml of dioxane, 0.80 g of the obtained 3-[5-bis (ethanesulfonyl)amino-2,4-dichlorophenyl]-1-methyl-6-trifluoromethyl-2,4 (1H,3H)-pyrimidinedione was dissolved and 0.12 g of sodium hydroxide (93%) and 2 ml of water were added to the obtained solution. After the mixed solution was stirred for 4 hours, a dilute hydrochloric acid was added thereto in order to acidify the resultant solution. The reaction mixture was extracted with ethyl acetate. The obtained extract of the ethyl acetate layer was washed with water and a saturated sodium chloride aqueous solution, and dried over anhydrous sodium sulfate. Then ethyl acetate was distilled off to obtain a crude product. The obtained product was purified by preparative thin-layer chromatography (developing solvent: hexane/ethyl acetate=3/2) to obtain 0.46 g of the objective product as white crystals.

REFERENCE EXAMPLE 1

Synthesis of
3-[5-bis(methanesulfonyl)amino-4-chloro-2-fluorophenyl]-1-methyl-6-trifluoromethyl-2,4 (1H,3H)-pyrimidinedione (Intermediate)

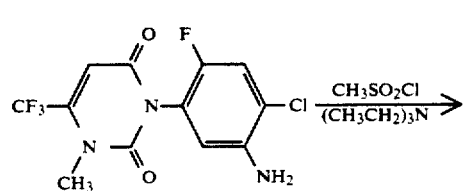

-continued

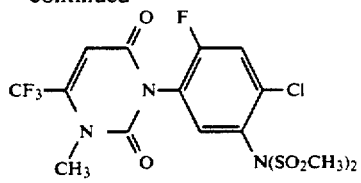

To a mixture of 1.00 g of 3-(5-amino-4-chloro-2-fluorophenyl)-1-methyl-6-trifluoromethyl-2,4 (1H,3H)-pyrimidinedione, 0.63 g of triethylamine and 10 ml of dichloromethane, 0.48 g of methanesulfonylchloride was added at a temperature of not more than 5° C. The resultant mixture was stirred overnight. After washing twice the reaction mixture with water, the reaction mixture was washed with a saturated sodium chloride aqueous solution and dried over anhydrous sodium sulfate. The dichloromethane was distilled off to obtain a crude product. The obtained product was washed with diisopropylether to obtain 1.36 g of the objective product as white crystals. m.p.: 282°~285° C.

$^1$H-NMR(d$_6$-DMSO) δ(ppm): 3.54(6H,s), 4.22(3H,s), 6.48(1H,s), 7.79(1H,d,J=9Hz), 7.98(1H,d,J=7Hz)

REFERENCE EXAMPLE 2

Synthesis of 3-[5-bis(methanosulfonyl)amino-2,4-dichlorophenyl]-1-methyl-6-trifluoromethyl-2,4 (1H,3H)-pyrimidinedione (Intermediate)

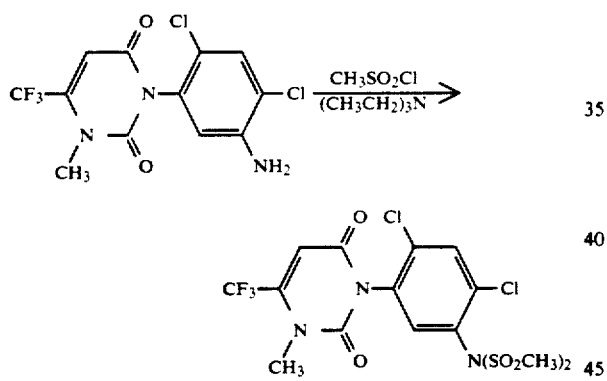

To a mixture of 1.00 g of 3-(5-amino-2,4-dichlorophenyl)-1-methyl-6trifluoromethyl-2,4 (1H,3H)-pyrimidicedione, 0.60 g of triethylamine and 10 ml of dichloromethane, 0.46 g of methanesulfonylchloride was added at a temperature of not more than 5° C. The resultant mixture was stirred overnight. After washing twice the reaction mixture with water, the reaction mixture was washed with a saturated sodium chloride aqueous solution and dried over anhydrous sodium sulfate. The dichloromethane was distilled off to obtain a crude product. The obtained product was washed with diisopropylether to obtain 1.40 g of the objective product as white crystals.

m.p.: not less than 300° C.

$^1$H-NMR(d$_6$-DMSO) δ(ppm): 3.50(6H,s), 4.20(3H,s), 6.35(1H,s), 7.55(1H,s), 7.65(1H,s)

The uracil derivatives of the present invention synthesized according to the above Examples and synthesized by following the similar procedures to the above Examples or Schemes are shown in Table 1, and the physical properties of these compounds are shown in Table 2.

Further, the uracil derivative of the present invention synthesized according to the above Examples and synthesized by following the similar procedures to the above Examples or Schemes are shown in Table 3. The compounds obtainable in accordance with the present invention, however, are not limited to those shown in the following tables.

TABLE 1

| Compound No. | Structure |
|---|---|
| 1 | ![structure] CF$_3$, O, N-CH$_3$, N, Cl, NSO$_2$CH$_3$, H |
| 2 | CF$_3$, O, N-CH$_3$, N, Cl, NSO$_2$C$_2$H$_5$, H |
| 3 | CF$_3$, O, N-CH$_3$, N, F, Cl, NSO$_2$CH$_3$, H |
| 4 | CF$_3$, O, N-CH$_3$, N, F, Cl, NSO$_2$C$_2$H$_5$, H |
| 5 | CF$_3$, O, N-CH$_3$, N, F, Cl, NSO$_2$CH(CH$_3$)$_2$, H |
| 6 | CF$_3$, O, N-CH$_3$, N, F, Cl, NSO$_2$(CH$_2$)$_2$CH$_3$, H |

TABLE 1-continued

| Compound No. | Structure |
|---|---|
| 7 | 2-F, 4-Cl-phenyl; NHSO$_2$(CH$_2$)$_3$CH$_3$; N-CH$_3$; CF$_3$ |
| 8 | 2,4-diCl-phenyl; NHSO$_2$CH$_3$; N-CH$_3$; CF$_3$ |
| 9 | 2,4-diCl-phenyl; NHSO$_2$CH$_2$CH$_3$; N-CH$_3$; CF$_3$ |
| 10 | 2-F, 4-Cl-phenyl; NHSO$_2$CH$_2$CF$_3$; N-CH$_3$; CF$_3$ |
| 11 | 2-F, 4-Cl-phenyl; NHSO$_2$CH$_2$CH$_2$CH$_2$Cl; N-CH$_3$; CF$_3$ |
| 12 | 2,4-diF-phenyl; NHSO$_2$CH$_2$CH$_3$; N-CH$_3$; CF$_3$ |
| 13 | 2-F, 4-Br-phenyl; NHSO$_2$CH$_2$CH$_3$; N-CH$_3$; CF$_3$ |

TABLE 2

| Compound No. | $^1$H-NMR δ (ppm) [solvent] | Physical Properties |
|---|---|---|
| 1 | 2.94(3H, s), 3.45(3H, s), 6.21(1H, s), 6.68~7.00(1H, m), 7.07~7.59(3H, m) [d$_6$-DMSO] | m.p.: 174~177° C. |
| 2 | 1.33(3H, t, J=7Hz), 3.12(2H, q, J=7Hz), 3.52(3H, s), 6.25(1H, s), 6.71~7.17(2H, m), 7.26~7.64(2H, m) [d$_6$-DMSO] | m.p.: 177~180° C. |
| 3 | 2.95(3H, s), 3.43(3H, s), 6.29(1H, s), 7.39(1H, d, J=9Hz), 7.44(1H, d, J=7Hz), 9.28(1H, br s) [d$_6$-DMSO] | m.p.: 168~171° C. |
| 4 | 1.32(3H, t, J=7Hz), 3.06(2H, q, J=7Hz), 3.43(3H, s), 6.23(1H, s), 7.29(1H, d, J=9Hz), 7.41(1H, d, J=7Hz), 9.11(1H, br s) [d$_6$-DMSO] | m.p.: 165~167° C. |
| 5 | 1.34(6H, d, J=7Hz), 3.22(1H, qq, J=7Hz), 3.48(3H, s), 6.22(1H, s), 6.90(1H, br s), 7.17(1H, d, J=9Hz), 7.56(1H, d, J=7Hz) [CDCl$_3$] | viscous oil |
| 6 | 1.00(3H, t, J=7Hz), 1.25~2.19(2H, m), 2.80~3.28(2H, m), 3.54(3H, s), 6.35(1H, s), 7.16(1H, br s), 7.40(1H, d, J=9Hz), 7.70(1H, d, J=7Hz) [CDCl$_3$] | m.p.: 113~115° C. |
| 7 | 0.70~2.19(7H, m), 2.88~3.24(2H, m), 3.49(3H, s), 6.22(1H, s), 6.91(1H, br s), 7.20(1H, d, J=8Hz), | m.p.: 115~117° C. |

TABLE 2-continued

| Compound No. | $^1$H-NMR δ (ppm) [solvent] | Physical Properties |
|---|---|---|
|  | 7.50(1H, d, J=7Hz) [CDCl$_3$] |  |
| 8 | 3.06(3H, s), 3.50(3H, s), 6.42(1H, s), 7.62(1H, s), 7.74(1H, s), 10.00(br s) [d$_6$-DMSO] | m.p.: 172~173° C. |
| 9 | 1.31(3H, t, J=7Hz), 3.10(2H, q, J=7Hz), 3.52(3H, s), 6.34(1H, s), 7.21(1H, s), 7.59(1H, s), 7.66(1H, s) [CDCl$_3$] | m.p.: 152.5~153.5° C. |
| 10 | 3.46(3H, s), 3.94(2H, q, J=9Hz), 5.15(1H, br s), 6.23(1H, s), 7.25(1H, d, J=9Hz), 7.40(1H, d, J=7Hz) [CDCl$_3$] | m.p.: 181~184° C. |
| 11 | 2.05-2.45(2H, m), 3.21(2H, t, J=8Hz), 3.47(3H, s), 3.61(2H, t, J=8Hz), 6.32(1H, s), 7.35(1H, d, J=8Hz), 7.36(1H, br s), 7.60(1H, d, J=7Hz) [CDCl$_3$] | vitrified |
| 12 | 1.34(3H, t, J=7Hz), ), 3.05(2H, q, J=7Hz), 3.47(3H, br s), 6.22(1H, s), 6.99(1H, dd, J=10Hz), 7.35(1H, dd, J=8Hz), 9.32(1H, br s), [d$_6$-DMSO] | m.p.: 183~186° C. |
| 13 | 1.35(3H, t, J=7Hz), ), 3.11(2H, q, J=7Hz), 3.54(3H, br s), 6.34(1H, s), 6.86(1H, br s), 7.50(1H, d, J=9Hz), 7.67(1H, d, J=7Hz), [CDCl$_3$] | m.p.: 136~140° C. |

TABLE 3

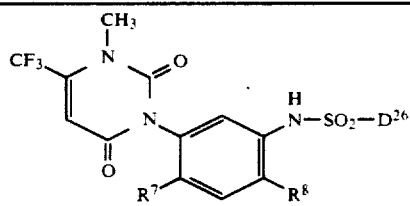

| R$^7$ | R$^8$ | D$^{26}$ |
|---|---|---|
| H | Cl | CH$_3$ |
| H | Cl | CH$_2$CH$_3$ |
| H | Cl | CH$_2$CH$_2$CH$_3$ |
| H | Cl | CH(CH$_3$)$_2$ |
| H | Cl | CH$_2$CH$_2$CH$_2$CH$_3$ |
| H | Cl | CH(CH$_3$)CH$_2$CH$_3$ |
| H | Cl | CH$_2$CH(CH$_3$)$_2$ |
| H | Cl | C(CH$_3$)$_3$ |
| H | Cl | CH$_2$CF$_3$ |
| H | Cl | CH$_2$CH$_2$CH$_2$Cl |
| Cl | Cl | CH$_3$ |
| Cl | Cl | CH$_2$CH$_3$ |
| Cl | Cl | CH$_2$CH$_2$CH$_3$ |
| Cl | Cl | CH(CH$_3$)$_2$ |
| Cl | Cl | CH$_2$CH$_2$CH$_2$CH$_3$ |
| Cl | Cl | CH(CH$_3$)CH$_2$CH$_3$ |
| Cl | Cl | CH$_2$CH(CH$_3$)$_2$ |
| Cl | Cl | C(CH$_3$)$_3$ |
| Cl | Cl | CH$_2$CF$_3$ |
| Cl | Cl | CH$_2$CH$_2$CH$_2$Cl |
| F | Cl | CH$_3$ |
| F | Cl | CH$_2$CH$_3$ |
| F | Cl | CH$_2$CH$_2$CH$_3$ |
| F | Cl | CH(CH$_3$)$_2$ |
| F | Cl | CH$_2$CH$_2$CH$_2$CH$_3$ |
| F | Cl | CH(CH$_3$)CH$_2$CH$_3$ |
| F | Cl | CH$_2$CH(CH$_3$)$_2$ |
| F | Cl | C(CH$_3$)$_3$ |
| F | Cl | CH$_2$CF$_3$ |
| F | Cl | CH$_2$CH$_2$CH$_2$Cl |
| F | F | CH$_3$ |
| F | F | CH$_2$CH$_3$ |
| F | F | CH$_2$CH$_2$CH$_3$ |
| F | F | CH(CH$_3$)$_2$ |
| F | F | CH$_2$CH$_2$CH$_2$CH$_3$ |

TABLE 3-continued

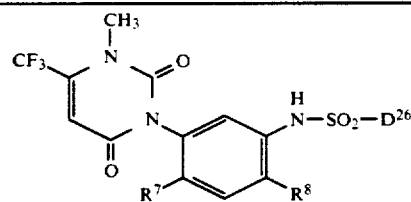

| R$^7$ | R$^8$ | D$^{26}$ |
|---|---|---|
| F | F | CH(CH$_3$)CH$_2$CH$_3$ |
| F | F | CH$_2$CH(CH$_3$)$_2$ |
| F | F | C(CH$_3$)$_3$ |
| F | F | CH$_2$CF$_3$ |
| F | F | CH$_2$CH$_2$CH$_2$Cl |
| H | F | CH$_3$ |
| H | F | CH$_2$CH$_3$ |
| H | F | CH$_2$CH$_2$CH$_3$ |
| H | F | CH(CH$_3$)$_2$ |
| H | F | CH$_2$CH$_2$CH$_2$CH$_3$ |
| H | F | CH(CH$_3$)CH$_2$CH$_3$ |
| H | F | CH$_2$CH(CH$_3$)$_2$ |
| H | F | C(CH$_3$)$_3$ |
| H | F | CH$_2$CF$_3$ |
| H | F | CH$_2$CH$_2$CH$_2$Cl |
| F | Br | CH$_3$ |
| F | Br | CH$_2$CH$_3$ |
| F | Br | CH$_2$CH$_2$CH$_3$ |
| F | Br | CH(CH$_3$)$_2$ |
| F | Br | CH$_2$CH$_2$CH$_2$CH$_3$ |
| F | Br | CH(CH$_3$)CH$_2$CH$_3$ |
| F | Br | CH$_2$CH(CH$_3$)$_2$ |
| F | Br | C(CH$_3$)$_3$ |
| F | Br | CH$_2$CF$_3$ |
| F | Br | CH$_2$CH$_2$CH$_2$Cl |
| H | Br | CH$_3$ |
| H | Br | CH$_2$CH$_3$ |
| H | Br | CH$_2$CH$_2$CH$_3$ |
| H | Br | CH(CH$_3$)$_2$ |
| H | Br | CH$_2$CH$_2$CH$_2$CH$_3$ |
| H | Br | CH(CH$_3$)CH$_2$CH$_3$ |
| H | Br | CH$_2$CH(CH$_3$)$_2$ |
| H | Br | C(CH$_3$)$_3$ |
| H | Br | CH$_2$CF$_3$ |
| H | Br | CH$_2$CH$_2$CH$_2$Cl |

TABLE 3-continued

[Structure: pyrimidinedione with CF₃, CH₃, N, O substituents and phenyl ring bearing R⁷, R⁸, and NH-SO₂-D²⁶ groups]

| R⁷ | R⁸ | D²⁶ |
|---|---|---|
| Cl | Br | CH₃ |
| Cl | Br | CH₂CH₃ |
| Cl | Br | CH₂CH₂CH₃ |
| Cl | Br | CH(CH₃)₂ |
| Cl | Br | CH₂CH₂CH₂CH₃ |
| Cl | Br | CH(CH₃)CH₂CH₃ |
| Cl | Br | CH₂CH(CH₃)₂ |
| Cl | Br | C(CH₃)₃ |
| Cl | Br | CH₂CF₃ |
| Cl | Br | CH₂CH₂CH₂Cl |

Shown below are the examples of formulations using the compounds of the present invention. It should be understood, however, that the formulations coming within the concept of the present invention are not limited to those shown below. In the following descriptions of Formulation Examples, all "parts" are by weight unless otherwise noted.

FORMULATION EXAMPLE 1

Wettable powder

| | |
|---|---|
| Compound 3 of the present invention | 50 parts |
| Zeeklite PFP (kaolin type clay, mfd. by Zeeklite Industries Co., Ltd.) | 43 parts |
| Sorpol 5050 (anionic surfactant, mfd. by Toho Chemical Co., Ltd.) | 2 parts |
| Runox 1000 C (anionic surfactant, mfd. by Toho Chemical Co., Ltd.) | 3 parts |
| Carplex #80 (anti-freezing agent) (white carbon, mfd. by Shionogi Pharm. Co., Ltd.) | 2 parts |

The above substances are uniformly mixed and ground to form a wettable powder.

FORMULATION EXAMPLE 2

Emulsifiable concentrate

| | |
|---|---|
| Compound 3 of the present invention | 3 parts |
| Xylene | 76 parts |
| Isophorone | 15 parts |
| Sorpol 3005 X (mixture of nonionic surfactant and anionic surfactant, mfd. by Toho Chemical Co., Ltd.) | 6 parts |

The above substances are uniformly mixed to prepare an emulsifiable concentrate.

FORMULATION EXAMPLE 3

Flowable

| | |
|---|---|
| Compound 3 of the present invention | 35 parts |
| Agrizole S-711 (nonionic surfactant, mfd. by Kao Corp.) | 8 parts |
| Runox 1000 C (anionic surfactant, mfd. by Toho Chemical Co., Ltd.) | 0.5 parts |
| 1% Rodopol water (thickener, mfd. by Rohone-Poulenc) | 20 parts |
| Ethylene glycol (anti-freezing agent) | 8 parts |
| Water | 28.5 parts |

The above substances are uniformly mixed to prepare a flowable.

FORMULATION EXAMPLE 4

Granules

| | |
|---|---|
| Compound 3 of the present invention | 0.1 parts |
| Bentonite | 55.0 parts |
| Talc | 44.9 parts |

The above substances are uniformly mixed and ground, then kneaded with stirring by adding a small amount of water, granulated by an extrusion granulator and dried to form granules.

FORMULATION EXAMPLE 5

Granular wettable powder (dry flowable)

| | |
|---|---|
| Compound 3 of the present invention | 75 parts |
| Isobam No. 1 (anionic surfactant, mfd. by Kuraray Isoprene Chemical Co., Ltd.) | 10 parts |
| Vanilex N (anionic surfactant, mfd. by Sanyo Kokusaku Pulp K. K.) | 5 parts |
| Carplex #80 (white carbon, mfd. by Shionogi Pharm. Co., Ltd.) | 10 parts |

The above substances are uniformly mixed and pulverized to form a dry flowable.

FORMULATION EXAMPLE 6

Wettable powder

| | |
|---|---|
| Compound 4 of the present invention | 50 parts |
| Zeeklite PFP (kaolin type clay, mfd. by Zeeklite Industries Co., Ltd.) | 43 parts |
| Sorpol 5050 (anionic surfactant, mfd. by Toho Chemical Co., Ltd.) | 2 parts |
| Runox 1000 C (anionic surfactant, mfd. by Toho Chemical Co., Ltd.) | 3 parts |
| Carplex #80 (anti-freezing agent) (white carbon, mfd. by Shionogi Pharm. Co., Ltd.) | 2 parts |

The above substances are uniformly mixed and ground to form a wettable powder.

FORMULATION EXAMPLE 7

Emulsifiable concentrate

| | |
|---|---|
| Compound 4 of the present invention | 3 parts |
| Xylene | 76 parts |
| Isophorone | 15 parts |
| Sorpol 3005 X (mixture of nonionic surfactant and anionic surfactant, mfd. by Toho Chemical Co., Ltd.) | 6 parts |

The above substances are uniformly mixed to prepare an emulsifiable concentrate.

FORMULATION EXAMPLE 8

Flowable

| | |
|---|---|
| Compound 4 of the present invention | 35 parts |
| Agrizole S-711 (nonionic surfactant, | 8 parts |

| | |
|---|---|
| mfd. by Kao Corp.) | |
| Runox 1000 C (anionic surfactant, mfd. by Toho Chemical Co., Ltd.) | 0.5 parts |
| 1% Rodopol water (thickener, mfd. by Rohone-Poulenc) | 20 parts |
| Ethylene glycol (anti-freezing agent) | 8 parts |
| Water | 28.5 parts |

The above substances are uniformly mixed to prepare a flowable.

FORMULATION EXAMPLE 9

Granules

| | |
|---|---|
| Compound 4 of the present invention | 0.1 parts |
| Bentonite | 55.0 parts |
| Talc | 44.9 parts |

The above substances are uniformly mixed and ground, then kneaded with stirring by adding a small amount of water, granulated by an extrusion granulator and dried to form granules.

FORMULATION EXAMPLE 10

Granular wettable powder (dry flowable)

| | |
|---|---|
| Compound 4 of the present invention | 75 parts |
| Isobam No. 1 (anionic surfactant, mfd. by Kuraray Isoprene Chemical Co., Ltd.) | 10 parts |
| Vanilex N (anionic surfactant, mfd. by Sanyo Kokusaku Pulp K. K.) | 5 parts |
| Carplex #80 (white carbon, mfd. by Shionogi Pharm. Co., Ltd.) | 10 parts |

The above substances are uniformly mixed and pulverized to form a dry flowable.

In practical use of the above formulations, in the case of wettable powder, emulsifiable concentrate, flowable and granular wettable powder, they ar diluted 50 to 1,000 times with water and then applied so that the active ingredient will be supplied at a rate of 0.0001 to 10 kg per hectare.

The utility of the compounds of the present invention as an active ingredient of herbicides will be clearly appreciated from the results of the test examples described below.

TEST EXAMPLE 1

Test on herbicidal effect by soil treatment

Sterilized diluvial soil was placed in a 15 cm × 22 cm × 6 cm plastic case. Then the seeds of barnyardgrass (*Echinochloa crus-galli*), crabgrass (*Digitaria adscendens*), annual sedge (*Cyperus microiria*), black nightshade (*Solanum nigrum*), hairly galinsoga (*Galinsoga ciliate*), fieldcress (*Rorippa indica*), rice (*Oryza sativa*), corn (*Zea mays*), wheat (*Triticum aestivum*), soybean (*Glycine max*) and cotton (*Cossipium herbaceum*) were sown mixedly in the case and covered up about 1 cm with soil, and then a test liquid herbicide was sprayed uniformly over the soil surface by a small-sized sprayer so that the active ingredient would be supplied at the predetermined rate. Each test liquid herbicide was prepared by diluting with water a formulation prepared according to the relevant Formulation Examples described above. Three weeks after application (spraying) of the test liquid herbicide, its herbicidal effects on said various species of weeds and crops were examined and evaluated according to the following standard ratings. The results are shown in Table 4.

Standard ratings

5: Growth control rate is more than 90%. (Plants were almost completely withered.)
4: Growth control rate is 70~90%.
3: Growth control rate is 40~70%.
2: Growth control rate is 20~40%.
1: Growth control rate is less than 5%. (Almost non-effective.)

The growth control rate was determined from the following formula after measuring the above-ground plant portion weight in the treated area and that in the nontreated area:

Growth control rate =

$$\left( 1 - \frac{\text{above-ground plant portion weight in treated area}}{\text{above-ground plant portion weight in non-treated area}} \right) \times 100$$

The underlined symbols in the table represent the following:

N: barnyardgrass (*Echinochloa crus-galli*)
M: crabgrass (*Digitaria adscendens*)
K: annual sedge (*Cyperus microiria*)
H: black nightshade (*solanum nigrum*)
D: hairly galinsoga (*Galinsoga ciliate*)
I: fieldcress (*Rorippa indicia*)
R: rice (*Oryza sativa*)
T: corn (*Zea mays*)
W: wheat (*Triticum aestivum*)
S: soybean (*Glycine max*)
C: cotton (*Cossipium herbaceum*)

TABLE 4

| Compound No. | Application amount (g/ha) | N | M | K | H | D | I | R | T | W | S | C |
|---|---|---|---|---|---|---|---|---|---|---|---|---|
| 1 | 10 | 0 | 0 | 2 | 4 | 5 | 5 | 0 | 0 | 0 | 0 | 0 |
|   | 20 | 1 | 1 | 3 | 5 | 5 | 5 | 0 | 0 | 0 | 0 | 0 |
|   | 40 | 2 | 2 | 4 | 5 | 5 | 5 | 0 | 0 | 0 | 0 | 1 |
| 2 | 10 | 0 | 0 | 2 | 3 | 5 | 5 | 0 | 0 | 0 | 0 | 0 |
|   | 20 | 1 | 1 | 3 | 4 | 5 | 5 | 0 | 0 | 0 | 0 | 0 |
|   | 40 | 2 | 2 | 4 | 5 | 5 | 5 | 0 | 0 | 0 | 0 | 1 |
| 3 | 10 | 5 | 5 | 5 | 5 | 5 | 5 | 4 | 0 | 0 | 0 | 1 |
|   | 20 | 5 | 5 | 5 | 5 | 5 | 5 | 5 | 1 | 0 | 0 | 2 |
|   | 40 | 5 | 5 | 5 | 5 | 5 | 5 | 5 | 2 | 1 | 0 | 5 |
| 4 | 10 | 5 | 3 | 5 | 5 | 5 | 5 | 0 | 0 | 0 | 0 | 2 |
|   | 20 | 5 | 4 | 5 | 5 | 5 | 5 | 1 | 0 | 0 | 0 | 4 |
|   | 40 | 5 | 5 | 5 | 5 | 5 | 5 | 3 | 0 | 0 | 0 | 5 |
| 5 | 10 | 4 | 4 | 5 | 5 | 5 | 5 | 1 | 1 | 0 | 0 | 4 |
|   | 20 | 5 | 5 | 5 | 5 | 5 | 5 | 2 | 2 | 0 | 0 | 5 |
|   | 40 | 5 | 5 | 5 | 5 | 5 | 5 | 4 | 3 | 1 | 0 | 5 |
| 6 | 10 | 3 | 2 | 5 | 5 | 5 | 5 | 1 | 0 | 0 | 0 | 4 |
|   | 20 | 4 | 4 | 5 | 5 | 5 | 5 | 2 | 1 | 0 | 0 | 5 |
|   | 40 | 5 | 5 | 5 | 5 | 5 | 5 | 4 | 2 | 1 | 0 | 5 |
| 7 | 10 | 3 | 4 | 5 | 5 | 5 | 5 | 0 | 0 | 0 | 0 | 2 |
|   | 20 | 4 | 5 | 5 | 5 | 5 | 5 | 1 | 1 | 0 | 0 | 3 |
|   | 40 | 5 | 5 | 5 | 5 | 5 | 5 | 2 | 2 | 1 | 0 | 4 |
| 8 | 20 | 5 | 5 | 5 | 5 | 5 | 5 | 4 | 0 | 0 | 0 | 1 |
|   | 40 | 5 | 5 | 5 | 5 | 5 | 5 | 5 | 1 | 0 | 0 | 2 |
|   | 80 | 5 | 5 | 5 | 5 | 5 | 5 | 5 | 2 | 1 | 0 | 5 |
| 9 | 20 | 5 | 3 | 5 | 5 | 5 | 5 | 0 | 0 | 0 | 0 | 2 |
|   | 40 | 5 | 4 | 5 | 5 | 5 | 5 | 1 | 0 | 0 | 0 | 4 |
|   | 80 | 5 | 5 | 5 | 5 | 5 | 5 | 3 | 0 | 0 | 0 | 5 |
| 10 | 10 | 4 | 4 | 5 | 5 | 5 | 5 | 1 | 1 | 0 | 0 | 3 |
|   | 20 | 5 | 5 | 5 | 5 | 5 | 5 | 2 | 2 | 0 | 0 | 4 |
|   | 40 | 5 | 5 | 5 | 5 | 5 | 5 | 4 | 3 | 1 | 0 | 5 |

TABLE 4-continued

| Compound No. | Application amount (g/ha) | N | M | K | H | D | I | R | T | W | S | C |
|---|---|---|---|---|---|---|---|---|---|---|---|---|
| 11 | 10 | 4 | 4 | 5 | 5 | 5 | 5 | 0 | 0 | 0 | 0 | 3 |
|  | 20 | 5 | 5 | 5 | 5 | 5 | 5 | 2 | 1 | 0 | 0 | 4 |
|  | 40 | 5 | 5 | 5 | 5 | 5 | 5 | 3 | 3 | 1 | 0 | 5 |
| 12 | 20 | 3 | 5 | 5 | 5 | 5 | 5 | 0 | 0 | 0 | 0 | 3 |
|  | 40 | 4 | 5 | 5 | 5 | 5 | 5 | 1 | 0 | 0 | 0 | 4 |
|  | 80 | 5 | 5 | 5 | 5 | 5 | 5 | 3 | 2 | 1 | 0 | 5 |
| 13 | 10 | 4 | 4 | 5 | 5 | 5 | 5 | 0 | 0 | 0 | 0 | 0 |
|  | 20 | 5 | 5 | 5 | 5 | 5 | 5 | 1 | 0 | 1 | 0 | 2 |
|  | 40 | 5 | 5 | 5 | 5 | 5 | 5 | 4 | 1 | 2 | 0 | 4 |

What is claimed is:

1. Uracil derivatives represented by the formula (I):

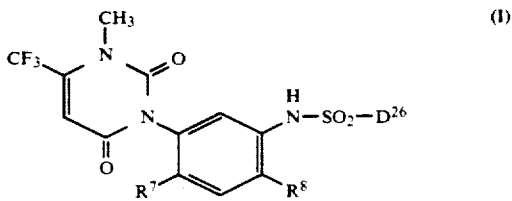

wherein $R^7$ represents hydrogen or halogen, $R^8$ represents halogen and $D^{26}$ represents $C_{1-4}$ alkyl or $C_{1-3}$ haloalkyl.

2. Uracil derivatives according to claim 1, wherein $R^7$ represents hydrogen, fluorine, chlorine and $R^8$ represents chlorine.

3. Uracil derivatives according to claim 1, wherein $D^{26}$ represents methyl, ethyl, n-propyl, iso-propyl, n-butyl, iso-butyl, sec-butyl, t-butyl, trifluoroethyl, chloro-n-propyl.

4. A herbicidal composition comprising a herbicidally effective amount of at least one of uracil derivatives as claimed in claim 1 and herbicidally acceptable carrier or diluent therefor.

5. A herbicidal composition according to claim 4 wherein said uracil derivative is a compound as claimed in claim 2.

6. A herbicidal composition according to claim 4, wherein said uracil derivative is a compound as claimed in claim 3.

7. A method for killing weeds or inhibiting growth of amount of an uracil derivative as claimed in claim 1.

8. A method according to claim 7, wherein said uracil derivative is a compound as claimed in claim 2.

9. A method according to claim 7, wherein said uracil derivative is a compound as claimed in claim 3.

10. A herbicidal composition having a selective killing activity of weeds or a selective inhibiting activity of the growth of the weeds in soybean growing sites without harming the soybean plant, which comprises a herbicidally effective amount of uracil derivatives as claimed in claim 1, #and a herbicidally acceptable carrier or diluent therefor.

11. A method for selectively killing weeds or selectively inhibiting the growth of the weeds in soybean growing sites without harming the soybean plant, which comprises applying a herbicidally effective amount of uracil derivatives as claimed in claim 1.

* * * * *

UNITED STATES PATENT AND TRADEMARK OFFICE
CERTIFICATE OF CORRECTION

PATENT NO. : 5,154,755

DATED : October 13, 1992

INVENTOR(S) : Jun SATOW, et al

Page 1 of 4

It is certified that error appears in the above-identified patent and that said Letters Patent is hereby corrected as shown below:

Column 1, line 15, "the present" should read
-- The present --.

Column 1, line 16, "having an" should read
-- having a --.

Column 1, line 29, "(foilage treatment)" should read
-- (foliage treatment) --.

Column 1, line 46, "as amount" should read
-- an amount --.

Column 1, line 62, " by one of herbicide is of wide "
should read -- by one herbicide are of a wide --.

Column 1, line 66, " of one of herbicides. " should read
-- of one of the herbicides. --.

Column 2, lines 12 and 13, " as one the herbicides " should
read -- as one of the herbicides --.

Column 2, line 30, " alkoxyalkyl or n " should read
-- alkoxyalkyl or --.

Column 2, line 67, " tri- or tetrametylene, " should read
-- tri- or tetramethylene, --.

UNITED STATES PATENT AND TRADEMARK OFFICE
CERTIFICATE OF CORRECTION

PATENT NO.  : 5,154,755

DATED       : October 13, 1992

INVENTOR(S) : Jun SATOW, et al

It is certified that error appears in the above-identified patent and that said Letters Patent is hereby corrected as shown below:

Column 3, line 27, " represent trior tetramethylene, " should read -- represent tri or tetramethylene, --.

Column 4, line 31, " against a vide variety of " should read -- against a wide variety of --.

Column 4, line 62, "represents C1-4 alkyl or C1-3" should read -- represents $C_{1-4}$ alkyl or $C_{1-3}$ -- .

Column 8, line 58, "without isolationthereof," should read -- without isolation thereof, --.

Column 10, line 53, " N,N-diethylanilin, " should read -- N,N-diethylaniline, --.

Column 13, line 21, "alkalis or acids is used in amount of" -- alkalis or acids are used in an amount of --.

Column 14, line 38, "acids is used" should read -- acids are used --.

Column 15, line 29, "*Veronic persica,*" should read -- *Veronica persica,* --.

Column 15, line 52, " do not harm to the " should read -- do not harm the --.

UNITED STATES PATENT AND TRADEMARK OFFICE
CERTIFICATE OF CORRECTION

PATENT NO. : 5,154,755

DATED : October 13, 1992

INVENTOR(S) : Jun SATOW, et al

It is certified that error appears in the above-identified patent and that said Letters Patent is hereby corrected as shown below:

Column 15, line 66, " compounds of present invention " should read -- compounds of the present invention --.

Column 16, line 55, "The compounds of present invention" should read --The compounds of the present invention--.

Column 16, line 61, "compounds of present" should read -- compounds of the present --.

Column 17, line 18, " a wise variety " should read -- a wide variety --.

Column 18, line 27, " was added an the resultant " should read -- was added and the resultant --.

Column 18, line 56, "to a suspension" should read -- To a suspension --.

Column 19, line 29, " isoporopylsulfonylaminophenyl]- " should read -- isopropylsulfonylaminophenyl]- --.

Column 20, line 15, " 1.48)6H,t,J=7Hz), " should read -- 1.48(6H,t,J=7Hz), --.

UNITED STATES PATENT AND TRADEMARK OFFICE
CERTIFICATE OF CORRECTION

PATENT NO. : 5,154,755

DATED : October 13, 1993

INVENTOR(S) : Jun SATOW, et al

It is certified that error appears in the above-identified patent and that said Letters Patent is hereby corrected as shown below:

Column 29, line 40, " they ar diluted " should read
    -- they are diluted --.

Column 32, line 15 and 16, "or inhibiting growth of amount of an uracil" should read -- or inhibiting growth of weeds, comprising applying a herbicidally effective amount of an uracil --.

Column 32, line 26, " in claim 1,#and a " should read
    -- in claim 1 and a --.

Signed and Sealed this

First Day of March, 1994

Attest:

BRUCE LEHMAN

Attesting Officer

Commissioner of Patents and Trademarks